(12) United States Patent
Guez

(10) Patent No.: US 8,868,190 B2
(45) Date of Patent: Oct. 21, 2014

(54) RECTAL STIMULATOR DEVICE AND USE THEREOF FOR THE TREATMENT OF RECTAL, FECAL AND/OR URINARY INCONTINENCE

(75) Inventor: Gérard Guez, Paris (FR)

(73) Assignee: Antemis, Celles-sur-Durolle (FR)

( * ) Notice: Subject to any disclaimer, the term of this patent is extended or adjusted under 35 U.S.C. 154(b) by 99 days.

(21) Appl. No.: 13/387,290

(22) PCT Filed: Jul. 29, 2010

(86) PCT No.: PCT/IB2010/001883
§ 371 (c)(1),
(2), (4) Date: Apr. 4, 2012

(87) PCT Pub. No.: WO2011/012992
PCT Pub. Date: Feb. 3, 2011

(65) Prior Publication Data
US 2012/0185014 A1    Jul. 19, 2012

Related U.S. Application Data

(60) Provisional application No. 61/229,897, filed on Jul. 30, 2009.

(51) Int. Cl.
*A61N 1/375*  (2006.01)
*A61N 1/36*   (2006.01)

(52) U.S. Cl.
CPC .................... *A61N 1/36007* (2013.01)
USPC .................... 607/41; 607/40; 607/138

(58) Field of Classification Search
USPC ................................. 607/41, 40, 138
See application file for complete search history.

(56) References Cited

U.S. PATENT DOCUMENTS

2009/0222058 A1*  9/2009  Craggs ..................... 607/41

FOREIGN PATENT DOCUMENTS

| WO | WO 2004/002572 A1 | 1/2004 |
| WO | WO 2007/104073 A1 | 9/2007 |

OTHER PUBLICATIONS

International Search Report and Written Opinion for International Application No. PCT/IB2010/001883, mailed Jan. 10, 2011.

* cited by examiner

*Primary Examiner* — Joseph Dietrich
(74) *Attorney, Agent, or Firm* — Alston & Bird LLP

(57) ABSTRACT

The invention relates to a rectal stimulator device for the treatment of rectal, fecal and/or urinary incontinence. The device comprises a) an ovoid-shaped stimulator provided with a microcontroller and an electronic circuit for receiving treatment instructions, electrodes for transmitting electrical pulses to the pelvic floor musculature and instructions to the microcontroller, and a battery and b) a stimulator grip member.

14 Claims, 1 Drawing Sheet

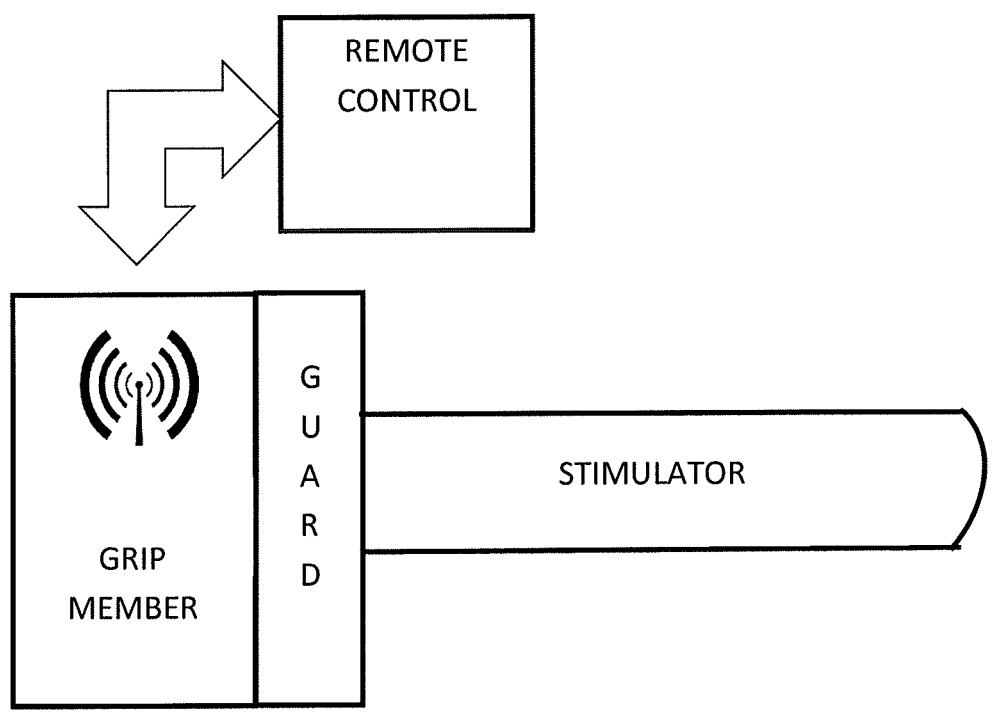

RECTAL STIMULATOR DEVICE AND USE THEREOF FOR THE TREATMENT OF RECTAL, FECAL AND/OR URINARY INCONTINENCE

CROSS REFERENCE TO RELATED APPLICATION

This application claims benefit of U.S. 61/229,897, filed Jul. 30, 2009, the entire contents of which is incorporated herein by reference.

FIELD OF THE INVENTION

The invention relates to a rectal stimulator device for the treatment of rectal, fecal and/or urinary incontinence.

BACKGROUND OF THE INVENTION

It is known that the continence organs are controlled by the pelvic floor muscles. These muscles support the viscera and are involved in sphincter function.

Changes in how they function result in problems which considerably affect the quality of life of the individuals concerned and represent significant expense for public health systems.

The interest in having means for maintaining continence and ensuring the well-being of the patients concerned can thus be understood.

SUMMARY OF THE INVENTION

Investigations in this field by the inventor have led him to develop a device capable of electrically stimulating the pelvic floor musculature in order to treat stress incontinence and also have a nervous reflex action providing rapid, effective treatment of urge incontinence.

The rectal stimulator device of the invention is characterised in that it includes:

a—an ovoid-shaped stimulator ensuring contact with the rectal mucosa, wherein the stimulator is provided with:
    a microcontroller and an electronic circuit capable of receiving treatment instructions,
    electrodes for transmitting the instructions to the microcontroller and for transmitting electrical pulses to the pelvic floor musculature; and
    a battery, advantageously a rechargeable battery;
b—a stimulator grip member, arranged at one end of the stimulator and configured so that the stimulator can be inserted into the anus of the patient in such a way as to ensure contact of the electrodes with the rectal mucosa.

BRIEF DESCRIPTION OF THE DRAWINGS

FIG. 1 is an illustration of a device in accordance with an embodiment of the present invention.

DETAILED DESCRIPTION OF THE INVENTION

Advantageously, the grip member comprises a guard to assist with the insertion of the stimulator prior to the treatment and with the removal thereof at the end of the treatment, while preventing the stimulator from completely entering the ampulla recti, the guard remaining outside the body.

Preferably, the electrodes are arranged on the surface of the stimulator and so positioned as to provide effective, but tolerable stimulations to the patient under treatment.

According to a first embodiment of the invention, the microcontroller receives the instructions via a remote control.

Accordingly, the invention relates more particularly to a device comprising a set of components, including:
a stimulator,
a grip member,
a guard,
as defined above, and
a remote control,
wherein the stimulator includes an antenna accommodated in the grip member which is connected to the stimulator, more particularly to the guard which co-operates with the remote control in such a way as to set the programme for a session depending on the rectal, fecal and/or urinary incontinence to be treated and to the duration of the session, and/or to transmit feedback information to a recorder, allowing both the practitioner and the patient to monitor the treatment. (See FIG. 1).

The antenna accommodated in the grip member receives instructions from the operator via a remote control and thus sets, in particular, the starting or stopping of the programme, the frequency and/or the working or duty cycle and/or the amperage between a null and a maximum value. If appropriate, the antenna transmits feedback information to a recorder. Since the antenna remains outside, the waves do not penetrate the patient's body.

In this embodiment, the stimulator has two electrodes on its surface.

Advantageously, the set of components according to this first embodiment of the invention further comprises a case including a compartment in which the stimulator can be secured in position, protected and transported without being damaged and also, if appropriate, a compartment for the remote control.

The case is connected to an AC power adapter and is provided with charge circuitry to recharge the battery of the stimulator when the latter is not in use.

According to a second embodiment of the invention, the treatment is preprogrammed and the microcontroller then receives instructions from a control case provided with an electronic control system for transmitting instructions given by the operator, without any cable linking the control case to the stimulator.

Advantageously, this case may contain a recorder for recording the parameters of use.

In this embodiment, the device essentially comprises a set of three components, namely a stimulator, a grip member with a guard and, advantageously, a control case including more particularly a compartment for the stimulator as defined in the first embodiment of the invention hereinabove.

The stimulator according to the second embodiment has three electrodes, i.e. two for transmitting the electrical pulses, and the third one for transmitting preprogrammed instructions to the microcontroller.

The use of the device of the invention as defined above and in the various embodiments thereof for the treatment of rectal, fecal and/or urinary incontinence also falls within the scope of the invention.

In particular, the invention relates to a method of treating rectal and/or urinary incontinence characterised by the use of such a device according to appropriate instructions, for a given type of incontinence.

Other features and advantages of the invention will become apparent from the following description of two particular embodiments thereof, which relate to a stimulator with a grip member and a guard, and a case for accommodating the stimulator.

The stimulator of the device of the invention, which is about 10 cm long, is generally ovoid. This shape is particularly suited to the anatomy of the patient and makes the stimulator more easily acceptable to him/her.

The stimulator is configured so that it can be inserted in such a way as to ensure contact of the electrodes with the rectal mucosa. Accordingly, it is possible to insert and position the stimulator in a given direction so as to achieve maximum contact with the mucosa and optimum safety for the physiological tissues.

According to the first embodiment of the invention, the stimulator has two electrodes on its surface for transmitting electrical pulses, arranged on both sides of the stimulator. The electrodes are adapted to be in contact with contacts arranged in the case.

The stimulator includes, at one of its ends, a guard which remains outside the body, thus preventing the stimulator from completely entering the ampulla recti by securing it in the desired position. Advantageously, the guard comprises a grip member which assists with the insertion or removal of the stimulator and which accommodates the antenna.

In the second embodiment of the invention, the stimulator has a third electrode for transmitting preprogrammed instructions to the microcontroller.

In comparison with the 10 cm-long stimulator, in these embodiments, the electrodes are arranged on the first two thirds of the stimulator, on the guard side, thus ensuring maximum contact with the mucosae and guaranteeing the effectiveness of the treatment.

The case comprises a base, a flap cover and, if appropriate, in both embodiments, a recorder.

The base, made from a rigid material, includes a compartment for the stimulator with the guard, another compartment for the remote control, and two opposite lateral flanges.

The thus-formed structure is lined with a liner, made from a flexible material, provided with a saddle-shaped cavity conforming to the compartment(s). With such arrangements, correct positioning of the stimulator and, if appropriate, of the remote control in the case is achieved.

The compartment(s) are shaped in such a way as to wedge and secure in place with no stress the stimulator and, if appropriate, the remote control.

Optionally, a pressure part arranged on the inside of the flap cover is so positioned on the flap that, when the latter is closed, it presses on the stimulator. This pressure part thus helps maintain the stimulator in the right position and also ensures correct contact between the electrodes of the applicator and the contacts arranged in the compartment. The components of the case, in particular the stimulator, may then be transported without risk of damage.

The case is closed by folding the cover down onto the base.

In the two embodiments of the invention, knobs, respectively (−;+), for controlling the work programme and opalescent areas may advantageously be provided on the surface of the base. These knobs and opalescent areas are easy to identify on the liner. The patient simply needs to press the marks corresponding to the knobs to adjust the current level as desired, using the opalescent area to visualise current variations.

Accordingly, the invention provides an effective rectal stimulator device which is practical to use. After several sessions, as prescribed by the practitioner, the patient rapidly notices an improvement in his/her condition with a reduction in the loss of urine and/or feces and/or gases and/or liquids and/or solids until there is absolutely none at all.

The invention claimed is:

1. A rectal stimulator device for the treatment of rectal, fecal and/or urinary incontinence, comprising:
    a—an ovoid-shaped stimulator ensuring contact with the rectal mucosa, wherein the stimulator is provided with:
        a microcontroller and an electronic circuit capable of receiving treatment instructions,
        electrodes for transmitting electrical pulses to the pelvic floor musculature and for transmitting the instructions to the microcontroller; and
        a battery;
    b—a stimulator grip member, arranged at one end of the stimulator and configured so that the stimulator can be inserted into the anus of the patient in such a way as to ensure contact of the electrodes with the rectal mucosa, the grip member being designed for remaining outside the body when the device is positioned in the anus of the patient, said grip member accommodating an antenna so that the antenna also remains outside the body when the device is positioned in the anus of the patient, wherein the antenna is configured to co-operate with a remote control to prevent the generation of waves inside the body.

2. The device according to claim 1, wherein the grip member comprises a guard to assist with the insertion of the stimulator prior to the treatment and with the removal thereof at the end of the treatment, while preventing the stimulator from completely entering the ampulla recti, the guard remaining outside the body.

3. The device according to claim 1, wherein the electrodes are arranged on the surface of the stimulator.

4. The device according to claim 1, wherein the microcontroller receives the instructions via the remote control.

5. The device according to claim 4, wherein the antenna accommodated in the grip member cooperates with the remote control in such a way as to set the program for a session depending on the rectal, fecal and/or urinary incontinence to be treated and to the duration of the session, and/or to transmit feedback information to a recorder.

6. The device according to claim 5, wherein the antenna accommodated in the grip member receives instructions from the operator and thus sets, in particular, the starting or stopping of the programme, the frequency and/or the working or duty cycle and/or the amperage between a null value and a maximum value.

7. The device according to claim 4, wherein the stimulator has two electrodes on its surface.

8. The device according to claim 4, wherein the device further comprises a case including a compartment in which the stimulator can be secured in position, protected and transported without being damaged.

9. The device according to claim 8, wherein the case contains a recorder for recording the parameters of use.

10. The device according to claim 1, wherein the microcontroller receives instructions from a control case provided with an electronic control system for transmitting preprogrammed instructions, without any cable linking the control case to the stimulator.

11. The device according to claim 10, wherein the device comprises a set of components, including a stimulator with a grip member and a guard, and a control case including a compartment for the stimulator as defined, wherein the stimulator has three electrodes, i.e. two for transmitting electrical pulses, and the third one for transmitting preprogrammed instructions to the microcontroller.

12. The device according to claim 10, wherein said case contains a recorder for recording the parameters of use.

13. The device according to claim 10, wherein the control case includes a compartment for the stimulator.

14. A method for the treatment of rectal, fecal and/or urinary incontinence, comprising the steps of:
    a—inserting a rectal stimulator device in the anus of the patient prior to treatment, said device comprising:
        an ovoid-shaped stimulator ensuring contact with the rectal mucosa, wherein the stimulator is provided with a microcontroller and an electronic circuit capable of receiving treatment instructions, electrodes for transmitting electrical pulses to the pelvic floor musculature and for transmitting the instructions to the microcontroller, and a battery;

a stimulator grip member, arranged at one end of the stimulator and configured so that the stimulator can be inserted into the anus of the patient in such a way as to ensure contact of the electrodes with the rectal mucosa, the grip member being designed for remaining outside the body when the device is positioned in the anus of the patient, said grip member accommodating an antenna so that the antenna also remains outside the body when the device is positioned in the anus of the patient, wherein the antenna is configured to co-operate with a remote control to prevent the generation of waves inside the body;

b—activating said rectal stimulator device for treatment; and c—removing said rectal stimulator device from the anus of the patient at the end of the treatment.

* * * * *